United States Patent [19]

Yudelson et al.

[11] Patent Number: 5,196,183

[45] Date of Patent: Mar. 23, 1993

[54] CONTRAST AGENTS FOR ULTRASOUND IMAGING

[75] Inventors: Joseph S. Yudelson; Susan E. Power, both of Rochester, N.Y.

[73] Assignee: Sterling Winthrop Inc., New York, N.Y.

[21] Appl. No.: 803,293

[22] Filed: Dec. 4, 1991

[51] Int. Cl.⁵ .................. A61K 49/00; A61B 8/12
[52] U.S. Cl. ........................... 424/9; 514/12; 514/13; 514/21; 514/558; 128/660.01; 128/662.02; 530/363; 530/427; 424/2
[58] Field of Search ............... 424/2, 9; 514/12, 13, 514/21, 558; 128/662.02, 660.01; 530/363, 427

[56] References Cited

U.S. PATENT DOCUMENTS

| | | | |
|---|---|---|---|
| 4,572,203 | 2/1986 | Feinstein | 128/661 |
| 4,718,433 | 1/1988 | Feinstein | 128/660 |
| 4,774,958 | 10/1988 | Feinstein | 128/660.01 |
| 4,832,941 | 5/1989 | Berwing et al. | 424/9 |
| 4,844,882 | 7/1989 | Widder et al. | 128/660.01 |
| 4,957,656 | 9/1990 | Cerny et al. | 128/660.02 |

FOREIGN PATENT DOCUMENTS 365467  4/1990  European Pat. Off. .

Primary Examiner—Glennon H. Hollrah
Assistant Examiner—Mark W. Russell
Attorney, Agent, or Firm—William J. Davis; Irving Newman

[57] ABSTRACT

Particles having an average diameter of less than about 12 microns comprising fatty acid cores encapsulated with human serum albumin and methods for their preparation are disclosed. These materials are useful as contrast agents in ultrasonic imaging, having scattering intensities that are equivalent to or greater than those obtain from dispersed microbubbles but being much more stable, both in storage and when used in vivo, than are contrast agents based on dispersed microbubbles.

27 Claims, No Drawings

CONTRAST AGENTS FOR ULTRASOUND IMAGING

FIELD OF INVENTION

The present invention related to the field of diagnostics imaging. More particularly, it relates to contrast agents for improving the images obtained when using the diagnostic imaging technique known as ultrasound imaging.

DESCRIPTION RELATIVE TO THE PRIOR ART

The examination of internal organs of humans and animals with ultrasound is a diagnostic method which was introduced some time ago and which is based on the reflection of ultrasonic waves in the megahertz range (above 1 MHz) at the interfaces between different types of tissue. The echoes thus produced are amplified and displayed. Particularly important in this connection is contrast medium echocardiography, which is used for the diagnosis of cardiopathies both in the M-mode and in two-dimensional echocardiography.

Ultrasonic imaging involves the transmission of ultrasonic energy through a substance whose acoustic properties are such that a portion of the directed ultrasonic radiation is reflected (scattered) and is received by a probe which is placed on the surface over the area to be imaged. The intensity of the scattered radiation is greatly dependent on the size of the scattering centers and the difference in density and compressibility between the scattering centers and the surrounding medium. The resulting images, that are obtained by transformation of the scattered ultrasonic radiation into electrical signals which are displayed on a screen, often lack sharpness and clarity. Therefore, a great deal of effort has been directed towards the design of biocompatible contrast agents which, when injected into the blood stream, will increase the intensity of the scattered radiation and, therefore, the sharpness and clarity of the resulting image, thereby facilitating enhanced ability to observe the flow of blood through the passages of the heart and other organs.

Various contrast media for ultrasonic echocardiography have already been described, such as unstabilized hydrogen peroxide, unstabilized sodium chloride solution enriched with carbon dioxide, gelatin-encapsulated microbubbles and microbubbles stabilized in other ways. See U.S. Pat. Nos. 4,572,203; 4,718,433; 4,774,958; and 4,844,882. Heretofore, such agents all have consisted of stabilized (or unstabilized) microbubbles.

ALBUNEX, which is sold by Molecular Biosystems, consists of microbubbles prepared by sonicating a solution of human serum albumin (HSA). Other systems that are under investigation in Europe include ECHOVIST and LEVOVIST, imaging agents comprising a galactose particle suspension which contains a quantity of entrapped air bubbles. All of these bubble systems suffer from instability when subjected to pressures that approximate the systolic blood pressure, i.e. 130 mm-Hg or greater. Meltzer and co-workers have shown that HSA microbubbles have a lifetime of 10 sec at 120 mm-Hg and that ECHOVIST loses half of its activity in 1-2 minutes. Higher pressures cause the rates to increase dramatically. Meltzer, R. S., et al, Advances in Echocardiography Conference, Oct. 4-5, 1990, Chicago, Ill.

There is need for an ultrasound contrast agent which is resistant to the pressures that are found in the blood stream. Such a material would enable one to visualize tissue and organs that previously have been inaccessible to the bubble containing contrast agents described above, as, for example in the visualization of blood perfusion through the heart, liver and other organs after the contrast agent has been injected into a distant peripheral vein or artery. It is also necessary that the contrast agent be composed of biocompatible materials and have a particle size distribution such that the agent will readily pass through the capillary beds of the lungs.

SUMMARY OF THE INVENTION

We have discovered that it is possible to prepare particles consisting of human serum albumin (HSA) and fatty acids that possess very great stability towards the pressures found in the blood stream. These particles scatter ultrasonic radiation at levels that are similar to or greater than those obtained with the microbubble materials that are presently available. More particularly, the present invention provides ultrasound imaging agents comprising fatty acid cores encapsulated with human serum albumin.

In another aspect, the present invention provides a method for preparing ultrasound imaging agents, this method comprising (a) preparing a fatty acid solution by dissolving a fatty acid in a solvent, (b) mixing the fatty acid solution with an HSA solution to form a dispersion of fine particles of the fatty acid coated with HSA; and (c) heating the resultant dispersion to a temperature above 90° C. while rapidly stirring to coagulate the HSA. The heating cross-links the albumin molecules into stable networks and drives off any low-boiling (organic) solvent that may have been used. While an organic solvent that is water miscible is generally chosen, it is possible to use nonwater-miscible solvents.

In an alternative method of the present invention, the fatty acid dispersion is prepared by acidifying a solution of a salt, typically the sodium salt, of the fatty acid to form an emulsion of the fatty acid. Then the HSA is added, followed by heating to coagulate the HSA. In this method, the use of a solvent for the fatty acid is obviated.

DETAILED DESCRIPTION OF THE INVENTION

The imaging agents of the present invention should have an average diameter in the range of 0.1 to 12 microns, preferably 0.1 to 10 microns, more preferably 0.1 to 8 microns.

The fatty acid that may be used to form the imaging agents of the present invention is selected from the fatty acids having from 6 to 18 carbon atoms. It may be saturated [$CH_3(CH_2)_n COOH$ wherein n is an integer from 4 to 16] or unsaturated, straight or branch chained. Preferably it is liquid at body temperature (32° C.). Also suitable is a mixture of fatty acids. While such mixtures may include fatty acids that are normally solid at 32° C., as well as fatty acids that are normally liquid at 32° C., it is preferred that the mixture be liquid at 32° C.

Examples of suitable fatty acids for use in preparing the imaging agents of the present invention include caproic acid, myristic acid, oleic acid, hexanoic acid, stearic acid, caprylic acid, isostearic acid, palmitic acid and lauric acid.

The fatty acid portions of the imaging agents of the present invention may contain up to 50% by weight, based on the weight of the fatty acid(s), of a physiologically compatible adjuvant, preferably an adjuvant that is liquid at 32° C. Such adjuvants may include oils, e.g. cholesterol, and surface active agents. They may have the effects of increasing echogenicity, controlling particle size, etc.

Also, the HSA may be modified, as by the attachment of polyalkylene glycol, in order to prevent immune response or increase the residence time of the agent in the organ.

It is also preferred that the ratio of the HSA portion to the fatty acid portion in the imaging agent particles of the present invention be from about 10:1 to about 1:1 by weight, preferably from 6:1 to 3:1, more preferably about 4:1.

In one method of the present invention, the imaging agent of the invention is prepared by precipitating the fatty acid in an HSA solution and then heating to coagulate the HSA. Sufficient stirring or agitation takes place during this process to assure an acceptable particle size distribution. In one preferred embodiment of this method, the precipitation is performed by injecting fatty acid solution into an HSA solution while using a sonicator to provide the desired agitation. While any suitable stirring speed may be used, we prefer to use a speed in the range of 60 to 600 RPM. We have also found that the degree of echogenicity may increase with increasing stirring speeds.

In an alternative method of the present invention, the imaging agent of the invention is prepared by first creating an aqueous dispersion of the fatty acid, as by acidifying a solution of the sodium salt of the acid, then mixing the dispersion with HSA, followed by heating to coagulate the HSA.

In one preferred embodiment of this method, a gas is bubbled through the fatty acid dispersion prior to mixing it with the HSA in order to enhance the echogenicity of the resulting particles. Preferably the gas is oxygen, although other biologically acceptable gases may be used. In this embodiment, the gas is preferably bubbled through the dispersion for at least 8 hours, more preferably at least 24 hours. In one trial (see Example 6), bubbling oxygen through the dispersion for 6 days was found to substantially enhance echogenicity.

Preferably, the heating step after precipitation is gradual, and is continued for at least about 45 minutes, more preferably at least one hour.

In practice, the imaging agent is generally injected into the subject in the form of a dispersion of the particles of the invention in a physiologically acceptable liquid, the dispersion generally having a percentage of solids of 0.1 to 3% (wt./vol), preferably from 0.1 to 2%, more preferably about 1.5% wt./vol.

EXAMPLE 1

Preparation of an Ultrasonic Contrast Agent Consisting of HSA and Myristic Acid 3.5 mL of a 7% solution of myristic acid dissolved in tetrahydrofuran was injected into 25 mL of a 2% solution of human serum albumin while the solution was exposed to the output of a Heat Systems WP 375 sonicator. The resultant dispersion was sonicated for 3 minutes, after which time the temperature was 51° C., which is well below the coagulation temperature of HSA. The dispersion was then heated with stirring (approximately 60 RPM) to the point where the temperature reached approximately 95° C. The total time consumed by the heating step was about 55 minutes. At this point, the dispersion was substantially free of tetrahydrofuran and had a translucent appearance. The particles had an average diameter of about 6 microns. A sample of this dispersion was examined at 7 Mhz radiation, and it gave a very good scattering (echogenicity) level of approximately 11 MV (millivolts). This is at least one order of magnitude greater than that of water.

EXAMPLE 2

Use of High Stirring Speeds

Repetition of the preparation of an HSA/myristic acid imaging agent following the procedure described in Example 1 gave an imaging agent having an echogenicity level of 19 mV. A similar preparation was carried out in which the stirring speed was raised by an order of magnitude (from about 60 RPM to about 600 RPM). This involved the whipping in of a large quantity of air. Large, entrapped air bubbles were eliminated by allowing the dispersion to stand for 24 hours, by which time the large bubbles had risen to the top of the liquid, following which the sample to be tested was withdrawn from the bottom of the container. The echogenicity level of this preparation was 57 mV. As noted above, care was taken so that this measurement did not occur by virtue of large entrapped bubbles. Microscopic examination at 3000 diameters failed to show the existence of bubbles. At this magnification, one should be able to discern bubbles that are greater than 0.2 micron in diameter. The particles had diameters in the range of from about 1 to 12 microns. After 1 month storage at room conditions, the echogenicity was virtually the same (54 mV).

For comparison purposes, a 2% solution of HSA was rapidly stirred at about 600 RPM. Initially, it also showed high echogenicity values (over 50 mV) (immediately after stirring). However, the scattering intensity decreased rapidly with time so that in a matter of minutes, signals were obtained that were barely above background (about 2 mV).

EXAMPLE 3

Preparation of HSA/Fatty Acid Contrast Agents Using Different Fatty Acids

Following the method described in Example 1, dispersions of HSA with the following fatty acids were prepared: palmitic, oleic, lauric, and stearic. All of them showed very high (greater than 30 mV) echogenicities.

EXAMPLE 4

Use of a Non-Water Miscible Organic Solvent

A dispersion of HSA/myristic acid was prepared as described in Example 1, but with the use of hexane in place of tetrahydrofuran. In this way, an oil in water emulsion is formed when the hexane solution is mixed with the HSA. Subsequent heating drives off the hexane, and leaves the fatty acid dispersed in the HSA. A dispersion prepared in this manner, having a concentration of about 1.9% solids, showed essentially the same echogenicity levels as obtained when tetrahydrofuran was used (27 mV).

EXAMPLE 5

Alternative Preparation (Without the Use of an Organic Solvent)

A 50 mL sample of a 0.5% solution of sodium oleate in water was titrated with 0.1N HCl so that the final pH was 3.5. The solution had become very turbid due to the formation of an oleic acid suspension. The particle size as measured by optical microscopy was in the 0.1 micron range.

A 30% aqueous solution of human serum albumin was added to this emulsion so that the final concentration of albumin was 2.0%. This mixture was then heated with moderate stirring over a 60 minute period so that the final temperature was 94° C. The echogenicity was measured to be 15.9 mV as compared with water (1.2 mV).

EXAMPLE 6

The Use of Oxygen to Enhance Echogenicity

An oleic acid emulsion was prepared as described in Example 5, and pure oxygen was bubbled through it for 6 days. Human serum albumin was added as described above, and the mixture heated with moderate stirring for 30 minutes, at the end of which time the temperature was 94° C. The echogenicity was measured as 93 mV as compared with water (1.2 mV).

While not wishing to be bound to any theory of the invention, it is noted that oxygen is readily absorbed by oleic acid. It is conceivable that, during heating, the dissolved oxygen is adsorbed onto the surface of the oleic acid, where it is entrapped by the albumin that is encapsulating the oleic acid (due to heating above its coagulation temperature). These gas bubbles are postulated to be very small (not visible at 3000x) and, evidently, very stable in the imaging agent. It is conceivable that other gases, such as argon, nitrogen, carbon dioxide, krypton, and nitrous oxide will have similar effects.

Thus, it is also possible that, even without the oxygen enhancement technique of this example, the echogenicity of the imaging agent particles of the present invention is due to encapsulated oxygen microbubbles, probably entrapped at the interface between the fatty acid and the HSA.

EXAMPLE 7

Effect of Dilution

A dispersion was prepared as described in Example 6. It showed an average particle size of 8 microns. The echogenicity at 2.5% solids was 35 mV. It was diluted to one-half the original concentration by the addition of water and the echogenicity measured. This dilution was repeated until the final concentrate was 1/32 of the original. The data for this series of experiments is shown below:

| Concentration | Echogenicity (mV) |
|---|---|
| 2.5% | 35 |
| 1.25% | 87 |
| 0.625% | 78 |
| 0.31% | 27 |
| .155% | 17 |
| .078% | 7.5 |

The data shows that this system retains good scattering levels at concentrations down to less than 0.1%.

EXAMPLE 8

Effect of adding a small amount of sodium oleate to the dispersion of oleic acid and HSA before heating A dispersion was prepared as described in Example 6. It showed a particle size of 6–10 microns. The echogenicity at 2.0% solids was 20 mV. Another dispersion was prepared in which a small amount of sodium oleate (2% by wt. of HSA) was added before heating. The echogenicity of this preparation was 36 mV at the same solids level and particle size.

EXAMPLE 9

Effect of Pressure

A sample of an HSA/palmitic acid particle dispersion prepared as described in Example 2 was subjected to a pressure of 160 mm-Hg for 30 minutes. The echogenicity showed little change before and after the application of pressure (70 mV in both cases). This demonstrates the stability of these contrast agents to pressure changes.

EXAMPLE 10

Effect of Diluting the Fatty Acid

A series of dispersions was made as described in Example 1, but in which part of the fatty acid, myristic acid in this case, was substituted by cholesterol, so that the ratios of cholesterol to myristic acid were 1:1, 2:1, and 1:2. Only the sample containing the high myristic acid levels showed high scattering levels. I.e., oils that are not fatty acids, e.g. cholesterol, do not have sufficient affinity to HSA to create stable echogenic particles. Rather, they act as diluents and can only be tolerated in minor proportions.

EXAMPLE 11

Effect of Substituting a Fatty Acid Alcohol (Comparative Example)

A dispersion was prepared as described in Example 1 but with the substitution of myristyl alcohol for the myristic acid. This alcohol is also known as 1-tetradecanol. The scattering level was much lower than that obtained with myristic acid, showing that fatty alcohols may not be substituted for fatty acids in the practice of this invention.

EXAMPLE 12

Substitution of Dextran for HSA

A dispersion was prepared as described in Example 1 but with the substitution of dextran polymer for the HSA. An excellent dispersion of myristic acid was produced, but very little echogenicity (2.8 mV) was obtained. This illustrates the uniqueness of HSA in the practice of this invention.

EXAMPLE 13

Control with No Fatty Acid

A control experiment was carried out in which the procedure of Example 1 was followed but with the omission of the fatty acid. No scattering was observed. This again shows the need for the fatty acid in this invention.

EXAMPLE 14

Demonstration of Left Side Imaging of the Heart

A dispersion prepared as described in Example 1 was injected into the right ventricle of a rabbit, and left heart imaging was observed, indicating that the contrast agent had migrated through the pulmonary capillary bed, through the lungs, and into the left ventricle. In addition, excellent liver profusion was observed from this same injection. Good left heart imaging results were also obtained when injection was done via the ear vein. These experiments were carried out at the Center for Pharmaceutical and Imaging Research at the Massachusetts General Hospital using 7.5 Mhz radiation and an Acuson Imager.

Variations and modifications can, of course, be made without departing from the spirit and scope of the invention.

We claim:

1. A diagnostic imaging agent comprising particles having an average diameter no larger than 12 microns, said particles comprising a core of one or more fatty acids encapsulated with human serum albumin.

2. The imaging agent of claim 1, wherein the average diameter of the particles is in the range of 0.1 to 12 microns.

3. The imaging agent of claim 2, wherein the average diameter is in the range of 0.1 to 10 microns.

4. The imaging agent of claim 3, wherein the average diameter is in the range of 0.1 to 8 microns.

5. The imaging agent of claim 1, wherein the fatty acid has from 6 to 18 carbon atoms.

6. The imaging agent of claim 5, wherein the fatty acid is saturated.

7. The imaging agent of claim 5, wherein the fatty acid is straight chained.

8. The imaging agent of claim 2, wherein the fatty acid is unsaturated.

9. The imaging agent of claim 5, wherein the fatty acid has a branched chain.

10. The imaging agent of claim 1, which further includes an adjuvant that is compatible with the fatty acid.

11. The imaging agent of claim 10, wherein the adjuvant is selected from physiologically acceptable oils and surfactants.

12. The imaging agent of claim 11, wherein the adjuvant is cholesterol.

13. The imaging agent of claim 10, wherein the adjuvant is present in an amount of from 0 to 50% by weight, based on the total weight of the fatty acid.

14. The imaging agent of claim 1, wherein the ratio of human serum albumin to fatty acid is from 10:1 to 1:1 by weight.

15. The imaging agent of claim 14, wherein said ratio is 4:1.

16. A method for preparing a diagnostic imaging agent comprising particles having an average diameter no larger than 12 microns, said particles comprising a core of one or more fatty acids encapsulated with human serum albumin, this method comprising forming a dispersion of fine particles of fatty acid coated with human serum albumin and heating the resultant dispersion to coagulate the human serum albumin.

17. The method of claim 16 wherein the dispersion is heated to a temperature above 90° C.

18. The method of claim 17 wherein the dispersion is heated for at least 45 minutes.

19. The method of claim 18 wherein the dispersion is heated for at least one hour.

20. The method of claim 16 wherein the dispersion is stirred at a speed in the range of 60 to 600 RPM.

21. The method of claim 16 which comprises the steps of (a) preparing a fatty acid solution by dissolving a fatty acid in a solvent, (b) mixing the fatty acid solution with a human serum albumin solution to form a dispersion of fine particles of the fatty acid coated with human serum albumin; and (c) heating the resultant dispersion to a temperature above 90° C. while rapidly stirring to coagulate the human serum albumin.

22. The method of claim 16 which comprises the steps of (a) acidifying a solution of a salt of the fatty acid to form an emulsion of the fatty acid, (b) adding the human serum albumin, and (c) heating to coagulate the human serum albumin.

23. The method of claim 22 wherein a gas is bubbled through the fatty acid solution prior to step (b).

24. The method of claim 23 wherein the gas comprises oxygen.

25. The method of claim 24 wherein the bubbling is conducted for at least 8 hours.

26. The method of claim 25 wherein the bubbling is conducted for at least 24 hours.

27. The method of claim 26 wherein the bubbling is conducted for 6 days.

* * * * *